United States Patent [19]

Burgoyne, Jr. et al.

[11] Patent Number: 5,055,616

[45] Date of Patent: Oct. 8, 1991

[54] ORTHO-ALKYLATED BISANILINES HAVING FLUORENYLIDENE BRIDGING GROUPS

[75] Inventors: William F. Burgoyne, Jr., Emmaus; Michael Langsam, Allentown, both of Pa.

[73] Assignee: Air Products and Chemicals, Inc., Allentown, Pa.

[21] Appl. No.: 472,001

[22] Filed: Jan. 29, 1990

[51] Int. Cl.$^5$ .................... C09B 11/02; B01D 53/22
[52] U.S. Cl. .................................. 564/322; 528/344
[58] Field of Search ........................................ 564/322

[56] References Cited

U.S. PATENT DOCUMENTS

| | | | |
|---|---|---|---|
| Re. 30,351 | 7/1980 | Hoehn | 55/16 |
| 2,083,890 | 6/1937 | Zerweck et al. | 564/322 |
| 3,822,202 | 7/1974 | Hoehn | 210/23 |
| 4,378,400 | 3/1983 | Makino et al. | 428/220 |
| 4,705,540 | 11/1987 | Hayes | 55/16 |
| 4,717,393 | 1/1988 | Hayes | 55/16 |
| 4,717,394 | 1/1988 | Hayes | 55/16 |
| 4,769,399 | 9/1988 | Schenz | 523/213 |

FOREIGN PATENT DOCUMENTS 203828 of 1986 European Pat. Off. .
62-112372 of 1988 Japan .

OTHER PUBLICATIONS

"Reverse Permselectivity of N$_2$ over CH$_4$ in Aromatic Polyimides", T. H. Kim et al., J. Appl. Poly. Sci., 34, pp. 1767–1771 (1987).
M. Salame, "Prediction of Gas Barrier Properties of High Polymers", Poly. Eng. Sci., Vol. 26, p. 1543 (1986).

*Primary Examiner*—C. Warren Ivy
*Assistant Examiner*—Raymond Covington
*Attorney, Agent, or Firm*—Keith D. Gourley; James C. Simmons; William F. Marsh

[57] ABSTRACT

Diamine compounds having the structural formula:

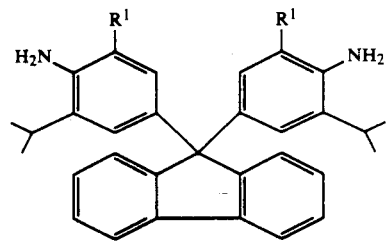

wherein R$_1$ is a methyl or ethyl group, can be used in preparing various polymers which are useful components in gas separation membranes. The combined effect of specific substituents ortho to the amino groups and the fluorenylidene bridging group imparts useful properties to polymeric membranes formed with these monomers.

3 Claims, No Drawings

ORTHO-ALKYLATED BISANILINES HAVING FLUORENYLIDENE BRIDGING GROUPS

TECHNICAL FIELD

The present invention relates to alkylated diamines which are useful in polymer preparations for gas membrane applications.

BACKGROUND OF THE INVENTION

There is a need for improved polymeric materials that are highly permeable, yet may under certain circumstances, provide selective separation of various gas combinations. Such materials would especially be useful in commercial, non-cryogenic gas separation processes.

The commercial application for gas separation devices based on polymeric materials relies, in part, on maximizing the overall gas flux through the membrane. P. H. Kim, et al., J. Appl. Poly. Sci., 34 1761 (1987), reported that the gas flux for a membrane is relatable to the average space between the polymer chains. In addition, they indicated that the density of the polymer is also related to the overall gas flux. The problem, in part, for these commercial applications is to identify polymers with very high flux and with good thermomechanical properties. It has generally been observed that to achieve high overall flux requires having a polymer with low chain-chain interactions. This can be exemplified by polymers such as poly(dimethylsiloxane) or poly(4-methyl-1-pentene). These materials have rather high gas flux values. These high flux materials have, because of their low chain-chain interaction, low glass transition temperatures (Tg). As a consequence, these materials require either special processing conditions to build in chemical and physiochemical crosslinking or they can be used only at rather low application temperatures. By contrast, polymers with strong chain-chain interactions have rather high Tg values and have usually exhibited rather low gas flux.

Polyimides, which generally have strong chain-chain interactions and have high Tg values, have been reported to have good gas flux values for certain specific structures. Specifically, U.S. Pat. Nos. 3,822,202 (1974); Re. 30,351 (1980) discloses a process for separating fluids using a semi-permeable membrane made from polyimides, polyesters or polyamides. The repeating units of the main polymer chain of these membranes are distinguished in that such repeating units have at least one rigid divalent subunit, the two main chain single bonds extending from which are not colinear, is sterically unable to rotate 360° around at least one of these bonds, and has 50% or more of its main chain atoms as members of aromatic rings.

U.S. Pat. No. 4,705,540 discloses a highly permeable aromatic polyimide gas separation membrane and processes for using said membrane. The membrane is an aromatic polyimide membrane in which the phenylenediamines are rigid and are substituted on a essentially all of the positions ortho to the amino substituents, and the acid anhydride groups are essentially all attached to rigid aromatic moieties.

U.S. Pat. Nos. 4,717,393 and 4,717,394 teach polymeric membranes and processes using the membranes for separating components of the gas mixture. The membranes disclosed in both of these patents are semi-flexible, aromatic polyimides, prepared by polycondensation of dianhydrides with phenylenediamines having alkyl substituents on all ortho positions to the amine functions, or with mixtures of other, non-alkylated diamines, some components have substituents on all positions ortho to the amine functions. It is taught that the membranes formed from this class of polyimides exhibit improved environmental stability and gas permeability, due to the optimization of the molecular free volume in the polymer. It is also taught that such membranes can be photochemically crosslinked, which in some instances results in a better performing membrane.

U.S. Pat. No. 4,378,400 discloses gas separation membranes formed from aromatic polyimides based upon biphenyltetra-carboxylic dianhydride for separating various gas mixtures.

M. Salame in Poly. Eng. Sci., 26 1543 (1986) developed a predictive relationship for oxygen permeability coefficient [(PO$_2$)] and polymer structure. In the publication he demonstrates the group contributions of various structural portions of a polymer to P(O$_2$) values. In particular he indicates the presence of an aromatic group, such as phenyl, in place of a methylene (—CH$_2$—) decreases the P(O$_2$) values for a pair of comparative polymers.

U.S. Pat. No. 4,769,399 discloses an adhesive composition which is the reaction product of an admixture of an effective amount of a phenoxy resin, at least one epoxy resin and a fluorene curative. Included as suitable fluorene curatives are compounds having the structural formula:

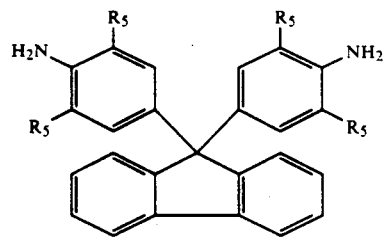

or

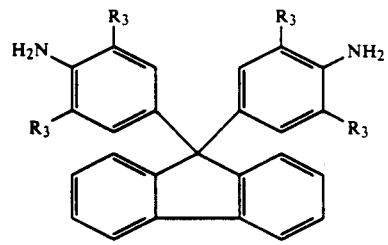

wherein R$_3$ and R$_5$ are independently —H or —CH$_3$.

European patent application 203828 (1986) discloses a fluorene compound for use in adhesives, which has the structural formula:

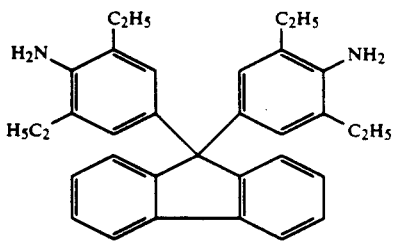

Japanese patent appliation 62-112372 discloses a polymeric membrane with an aromatic condensed polyimide as the film material. The polyimide is formed from diamines having the structural formula:

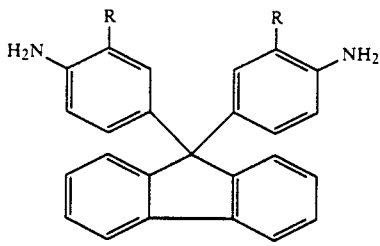

wherein R is H, CH$_3$ or C$_2$H$_5$.

SUMMARY OF THE INVENTION

Novel 9,9-bis(3-alkyl-4-amino-5-isopropylphenyl)fluorenes have been found which are useful in preparing various polymers for gas separation membranes. These diamine compounds can be represented by the structural formula:

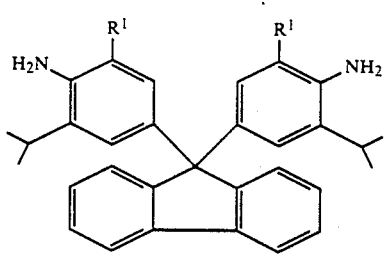

wherein R$_1$ is a methyl or ethyl group.

The presence of the optimum combination of a fluorene bridging group and the steric effects of specific alkyl groups ortho to the amine function, impart desirable properties to membranes formed from polymers prepared from these diamines. Specifically, such polymer membranes typically exhibit increased oxygen permeance, increased average main chain spacing and decreased average polymer density compared to membranes formed from similar polymers without these specific diamines.

DETAILED DESCRIPTION OF THE INVENTION

The present invention is drawn to novel 9,9-bis(3-alkyl-4-amino-5-isopropylphenyl)fluorenes represented by the structural formula:

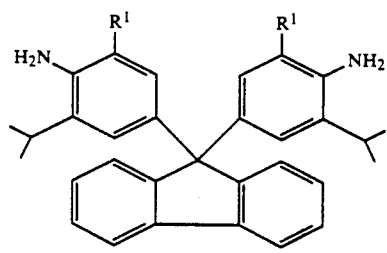

wherein R$_1$ is a methyl or ethyl group.

The above diamines, when polymerized with appropriate dielectrophiles, provide polymers which are useful as gas separation membranes. These diamines can be described as ortho-alkylated bisanilines wherein the bridging group is a fluorenylidene moiety. The combined effect of the specific substituents ortho to the amino groups along with the fluorenylidene bridging group results in diamine monomers which are extremely useful in polymer preparations for gas membrane applications. Polymers, such as polyimides, prepared from these diamines are effective as high flux gas separation membranes, in part, due to restricted rotation and/or low Van der Waal energy for the fluorenylidene bridging group and the steric bulk of the alkyl groups ortho to the diamine functional groups. These physical properties result in polymer membranes which exhibit high oxygen permeability, high average main chain spacing and decreased average polymer density when compared to similar polymers made from prior art diamines.

In the diamine structure, one ortho position to each amino group is an isopropyl group and the other ortho position is either a methyl or an ethyl group. In the case where the ortho positions are occupied by isopropyl and methyl groups, the diamine is 9,9-bis(3-methyl-4-amino-5-isopropylphenyl)fluorene, and when the ortho positions are occupied by isopropyl and ethyl groups, the diamine is 9,9-bis(3-ethyl-4-amino-5-isopropylphenyl)fluorene. A key feature of the diamine structure is the presence of an isopropyl group at one ortho position and an alkyl group at the second ortho position. It has been shown that if hydrogen is present at the second ortho position instead of an alkyl group, the diamine does not exhibit the desired properties. While it is believed that any alkyl group positioned at the second ortho position would result in diamines exhibiting the desired properties, attempts to synthesize diamines having isopropyl and higher alkyl groups at this position were unsuccessful. While these diamines are useful in forming polyimide gas separation membranes, they are also useful in forming other polymers for membrane and other applications, as well as for other uses, such as in adhesive compositions.

EXPERIMENTAL

Preparation of 9,9-bis(3-methyl-4-amino-5-isopropylphenyl)fluorene

The following procedure was used to prepare 9,9-bis(3-methyl-4-amino-5-isopropylphenyl)fluorene.

A 50.00 g (0.333 mol) portion of trifluoromethanesulfonic acid was slowly added to 261.2 g (1.75 mol) of 2-methyl-6-isopropylaniline contained in a one liter, three necked flask with mechanical stirring. After thorough mixing had occurred, 45.00 g (0.250 mol) of 9-fluorenone was added. The mixture was then heated to 155° C. for 17 hrs under an atmosphere of nitrogen with continuous stirring. After which time, the reaction vessel was fitted with a Claisen distillation head and the excess arylamine along with some of the acid were removed via vacuum distillation. The residual product was cooled below 80° C. then neutralized with a solution of 40.0 g (1.00 mol) of sodium hydroxide in 200 mL of water. The crude 9,9-bis(4-aminoaryl)fluorene was then isolated by extraction with several 800 mL volumes of toluene. Polymer grade diamine was obtained after recrystallization with toluene followed by vacuum drying at ca. 80°-100° C./5 mm Hg for 24 hours. The isolated yield of the diamine was 35.6% and a melting point range from 238°-241° C. The product provided satisfactory spectral and elemental analysis.

Reaction of 2,5-Diisopropylaniline with 9-Fluorenone in these examples were formed from polyimides having polymerizable units of the formula:

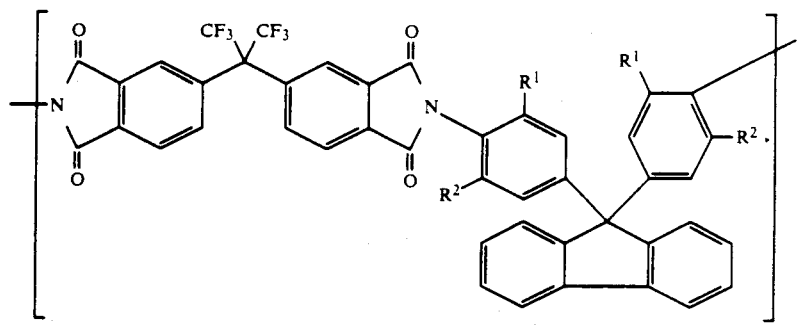

(Comparative)

The following procedure was carried out in an attempt to synthesize 9,9-bis(3,5-diisopropyl-4-aminophenyl)fluorene; i.e., isopropyl groups on both ortho position to each amino group.

A 100.00 g (0.468 mol) portion of 2,6-diisopropylaniline hydrochloride, 219 g (1.233 mol) of 2,6-diisopropylaniline, and 20.00 g (0.111 mol) of 9-fluorenone were combined in a one liter, three-necked flask fitted with a mechanical stirred and condenser. The mixture was heated to 150° C. for 20 hrs under an atmosphere of nitrogen with continuous stirring. After which time, the reaction vessel was fitted with a Claisen distillation head and the excess arylamine was removed via vacuum distillation. Following aqueous work-up, 28.7 g of a yellow compound (mp 121°-3° C.) was isolated which was found to have the structure 9-hydroxy-9-(3,5-diisopropyl-4-aminophenyl)fluorene. No. 9,9-bis(3,5-diisopropyl-4-aminophenyl)fluorene was detected. Similar results were obtained when trifluormethanesulfonic acid was used as acid catalyst. These results clearly indicate that, under these synthesis techniques, compounds having isopropyl groups on all four ortho positions to the amino groups could not be synthesized.

EXAMPLES 1-6

The diamine compounds of the present invention synthesized above were reacted with 6F-dianhydride to form polyimides in accordance with the procedures set out in U.S. patent application Ser. No. 07/316,214 now U.S. Pat. No. 4,897,092. Additionally, for comparative purposes, several prior art diamines were also reacted with 6F-dianhydride to form polyimides (Examples 2-6). The resultant polimides were cast as thin film membranes and tested for oxygen permeance ($P_{O_2}$) and $O_2/N_2$ selectivity ($\alpha O_2/N_2$). The results of these tests, along with the specific diamines used to form the polyimide are set out in Table 1 below. The membranes used

TABLE 1

| Example | DIAMINE $R^1$ | $R^2$ | $\overline{P}_{O_2}$ | $\alpha(O_2/N_2)$ |
|---|---|---|---|---|
| 1 | CH₃ | i-C₃H₇ | 87.4 | 4.16 |
| 2* | H | H | 11.7 | 3.90 |
| 3* | CH₃ | CH₃ | 60.1 | 3.63 |
| 4* | H | F | 1.2 | 4.0 |
| 5* | H | i-C₃H₇ | 16.8 | 5.1 |
| 6* | C₂H₅ | C₂H₅ | 37.6 | 3.67 |

*Comparative

From the results reported in Table 1 above, it is clearly shown that the diamines of the present invention can be used to form polyimide membranes which exhibit significantly higher oxygen permeance than polyimides formed from prior art diamines.

Having thus described the present invention, what is now deemed appropriate for Letters Patent is set out in the following appended claims.

What is claimed is:

1. A diamine having the structural formula:

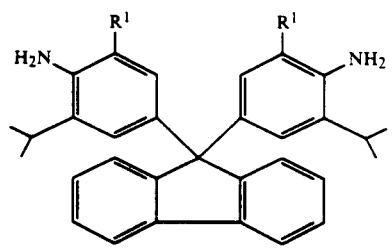

wherein $R_1$ is a methyl or ethyl group.

2. The compound 9,9-bis(3-methyl-4-amino-5-isopropylphenyl)fluorene.

3. The compound 9,9-bis(3-ethyl-4-amino-5-isopropylphenyl)fluorene.

* * * * *